(12) United States Patent
Arredondo

(10) Patent No.: US 9,539,463 B1
(45) Date of Patent: Jan. 10, 2017

(54) EXERCISE MAT

(71) Applicant: Andrew Arredondo, Tustin, CA (US)

(72) Inventor: Andrew Arredondo, Tustin, CA (US)

(*) Notice: Subject to any disclaimer, the term of this patent is extended or adjusted under 35 U.S.C. 154(b) by 0 days.

(21) Appl. No.: 15/060,472

(22) Filed: Mar. 3, 2016

Related U.S. Application Data

(60) Provisional application No. 62/176,923, filed on Mar. 3, 2015.

(51) Int. Cl.
| | |
|---|---|
| *A63B 5/22* | (2006.01) |
| *A63B 71/00* | (2006.01) |
| *A63B 24/00* | (2006.01) |
| *A63B 71/06* | (2006.01) |
| *A61B 5/00* | (2006.01) |
| *A61B 5/11* | (2006.01) |

(52) U.S. Cl.
CPC ......... *A63B 21/4037* (2015.10); *A61B 5/0002* (2013.01); *A61B 5/1123* (2013.01); *A61B 5/6892* (2013.01); *A61B 5/7278* (2013.01); *A61B 5/742* (2013.01); *A63B 24/0003* (2013.01); *A63B 24/0062* (2013.01); *A63B 71/0622* (2013.01); *A61B 2090/064* (2016.02); *A63B 2220/30* (2013.01); *A63B 2220/53* (2013.01)

(58) Field of Classification Search
CPC .......... A61B 5/22; A63B 71/00; A63B 15/02; A63B 26/00
USPC ............... 73/379.01, 379.04; 482/1, 8, 9, 23
See application file for complete search history.

(56) References Cited

U.S. PATENT DOCUMENTS

| | | | | |
|---|---|---|---|---|
| 4,702,475 A | * | 10/1987 | Elstein | A63B 69/0053 273/445 |
| 5,897,457 A | * | 4/1999 | Mackovjak | A63B 5/16 482/1 |
| 6,336,891 B1 | * | 1/2002 | Fedrigon | A63B 22/02 434/247 |
| 7,722,501 B2 | * | 5/2010 | Nicolas | A63B 23/0458 482/1 |
| 8,942,428 B2 | * | 1/2015 | Snook | G06F 3/011 382/103 |
| 2005/0264088 A1 | * | 12/2005 | Tadin | A47D 3/00 297/488 |
| 2008/0125290 A1 | * | 5/2008 | Cabados | A63B 6/00 482/23 |
| 2012/0058861 A1 | * | 3/2012 | Satut | A63B 21/4037 482/8 |
| 2012/0122636 A1 | * | 5/2012 | Shurtleff | A63B 21/4037 482/142 |
| 2016/0166876 A1 | * | 6/2016 | Goh | A63B 24/0062 482/9 |

\* cited by examiner

*Primary Examiner* — Jewel V Thompson
(74) *Attorney, Agent, or Firm* — John D. Tran; Rhema Law Group

(57) ABSTRACT

An example exercise mat is disclosed. The exercise mat comprises at least one sensor to detect an article on the mat and obtain a force measurement exerted by the article through a movement; and a communications unit to communicatively connect the mat to a computing device and provide the force measurement to the computing device. The computing device performs a plurality of calculations based on the force measurement.

14 Claims, 3 Drawing Sheets

EXERCISE MAT

CROSS REFERENCE TO RELATED APPLICATION

This application is a non-provisional application claiming the benefits of provisional application Ser. No. 62/176,923 filed on Mar. 3, 2015.

BACKGROUND

Conventional exercise mats are generally composed of a relatively firm padding enclosed in quilted covering material. The padding is usually thick and the quilted outer covering is thin and of durable wear-resistant material such as canvas or vinyl sheet. Such mats provide a reasonable degree of cushioning between typical hardwood flooring and the user which is sufficient for many exercises.

BRIEF DESCRIPTION OF THE DRAWINGS

Examples are described in the following detailed description and in reference to the drawings, in which.

DETAILED DESCRIPTION

Various aspects of the present disclosure are directed to an exercise mat. More specifically, and as described in greater detail below, various aspects of the present disclosure are directed to a multi-variable measurement exercise mat that is flexible, portable and contains an internal electrode assembly with multiple sensors embedded within the mat.

The following discussion is directed to various examples of the disclosure. Although one or more of these examples may be preferred, the examples disclosed should not be interpreted, or otherwise used, as limiting the scope of the disclosure, including the claims. In addition, one skilled in the art will understand that the following description has broad application, and the discussion of any example is meant only to be descriptive of that example, and not intended to intimate that the scope of the disclosure, including the claims, is limited to that example.

Figure 1:
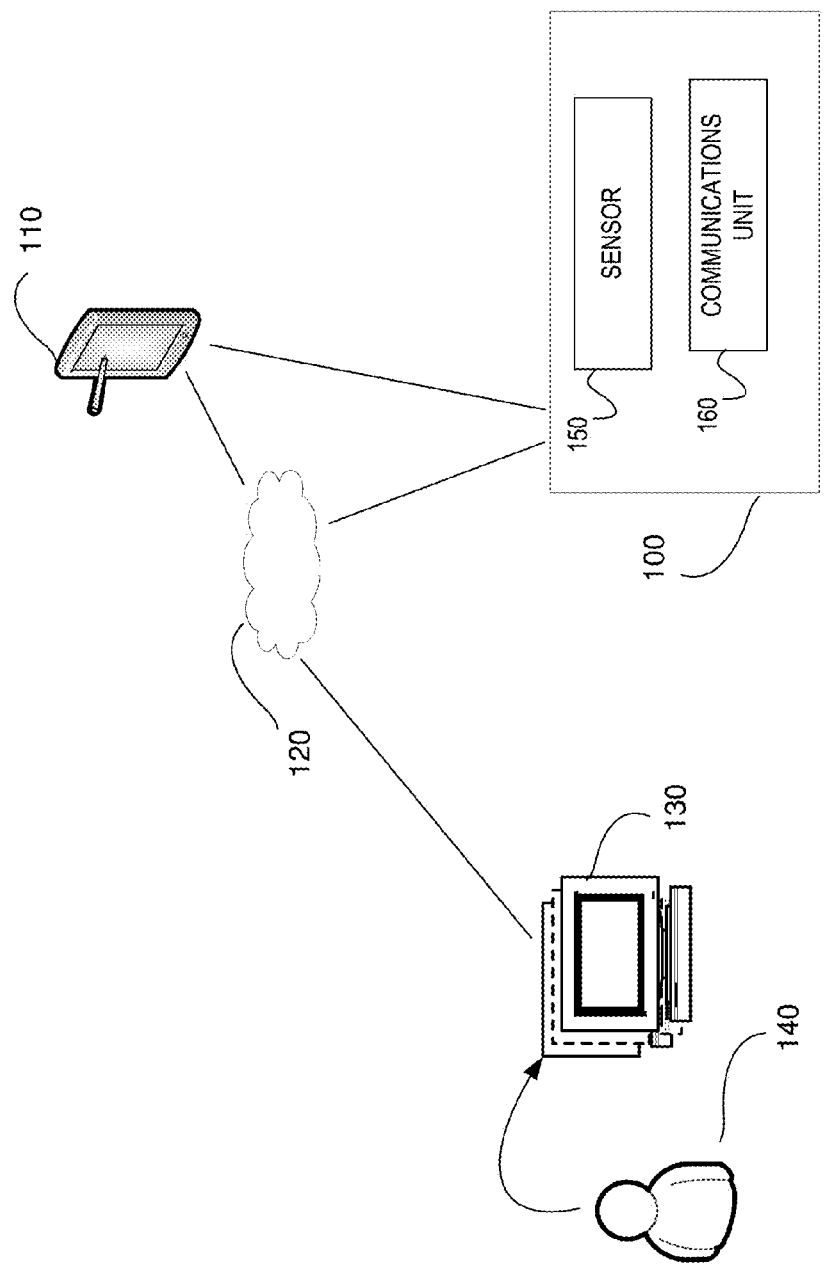
FIG. 1 illustrates a schematic representation of an exercise mat in accordance with an implementation of the present disclosure.

Referring now to FIG. 1, an exercise mat 100 in accordance with the principles disclosed herein is shown. The mat 100 may have a plurality of layers. More specifically, the mat 100 may have a bottom layer (downward facing) made up of rubber, providing texture to prevent sliding. In addition, the mat 100 may have a top later (upward facing) made up of rubber to provide durability. Further, the mat have a middle layer, comprising of an electronic circuitry including at least one sensor 150 and a communications unit 160. In one implementation, the mat 100 may be connected to a computing device. In another implementation, the mat 100 may comprise a processor (e.g., a central processing unit, a microprocessor, a microcontroller, or another suitable programmable device) and a memory unit of its own. Each of these components or any additional components of the mat 100 is operatively coupled to a bus. The bus may be any of several types of bus structures including a memory bus or memory controller, a peripheral bus, and a local bus using any of a variety of bus architectures. In other examples, the mat 100 includes additional, fewer, or different components for carrying out similar functionality described herein.

The mat 100 is connected to a computing device, which may comprise any suitable computing device while still complying with the principles disclosed herein. For example, in some implementations, the device may comprise a smartphone, a tablet, a phablet, an all-in-one computer (i.e., a display that also houses the computer's board), a smart watch or some combination thereof. In this example, the mat 100 is connected to a tablet 110 and a computer 130. In one implementation, the mat 100 and the computing devices may be connected via a wire. For example, the mat 100 and the tablet 110 are connected to each other through a wire. In another implementation, the mat 100 and the computing device may be connected wirelessly. For example, the mat 100 and the computer 130 are connected via the cloud. Further, the mat 100 may be connected to a display unit (not shown in FIG. 1). A user 140 of the mat 100 may use the display unit to interact with the mat 100. In other implementations, the display may be in the computing device (e.g., the computer 130 and/or the tablet 110). For example, the user may use the display in the computing device to control the mat 100.

In this implementation, the mat 100 is shown to be in a rectangular shape. In other examples, the mat 100 may have a different shape and size. For example, the mat 100 may be a square with measurements of 26 inches by 26 inches. In another example, the mat 100 may be a rectangular pad with measurements of 26 inches by 18 inches. In one implementation, the mat 100 is portable and may move with the user 140. In such an implementation, the mat 100 may have a thickness less than 1 inch and may weigh less than 15 pounds. In other examples, the mat 100 may have a permanent location in an environment (e.g., a room in a house). In either example, the mat 100 maintains connection with the computing device. When the mat 100 is powered/turned on, the mat 100 may confirm active connection with the computing device, detect an object or a person on the mat and proceed with measuring weight of the object or the product.

The computing device may include at least one processing resource. In examples described herein, a processing resource may include, for example, one processor or multiple processors included in a single computing device or distributed across multiple computing devices. As used herein, a "processor" may be at least one of a central processing unit (CPU), a semiconductor-based microprocessor, a graphics processing unit (GPU), a field-programmable gate array (FPGA) to retrieve and execute instructions, other electronic circuitry suitable for the retrieval and execution instructions stored on a machine-readable storage medium, or a combination thereof. As used herein, a "machine-readable storage medium" may be any electronic, magnetic, optical, or other physical storage apparatus to contain or store information such as executable instructions, data, and the like. For example, any machine-readable storage medium described herein may be any of a storage drive (e.g., a hard drive), flash memory, Random Access Memory (RAM), any type of storage disc (e.g., a compact disc, a DVD, etc.), and the like, or a combination thereof. Further, any machine-readable storage medium described herein may be non-transitory.

In one implementation, the computing device may comprise an application that works with the mat 100. For example, the mat 100 measures certain data related to the user 140, and the data measured is delivered to the application in the computing device. Further, various calculations may be performed by the application using the data received from the mat 100. For example, the application may calculate power and energy usage of the user 140 based on the data delivered to the computing device. In one implementation, the processor in the computing device may manage the operation of the application and displays the end results on the display unit (which can be a part of the computing device or separate from the computing device). More specifically, the processor receives a command from the user 140 to perform an action related to the mat 100. The user communicates the command by touching the instance window on the display. For example, the user 140 may touch an image of an application shown on the display of the device 110 to launch that application on that mobile device. The processor communicates the command received from the user to the device, and the device may launch the requested application. An updated instance may be provided to the display unit of the device 110, and the display unit may display an instance of the application, available for the user to operate.

The mat 100 comprises a sensor to measure and/or detect various parameters occurring on or near mat 100 during operation. In one implementation, the sensor measures data related to an object or person on the mat 100. More specifically, the sensor reads the force of impact on the mat 100. Such force of impact may be by a person (e.g., user 140) using an object or doing a motion (e.g., ball slams, battle ropes, sledgehammer hits, explosive pushups and squats). The mat sensors measure the amount of force of an individual applied through body weight movement and/or applied force through an object. Additionally, the mat 100 measures speed, strength and endurance of the user 140. Once this data is transferred to the computing device, the application may provide instant feedback for performance assessment for the user 140.

In another implementation, the sensor collects biometric data of the user 140 of the mat 100. The sensor may include any suitable biometric sensor configured to measure one or more of but is not limited to, heart rate, pulse rate, temperature, respiration, acceleration, skin resistivity, muscle contractions, and/or alike. In another implementation, more than one sensors may be provided. Each sensor may have a different resolution and field of view. Examples of applications in which the sensors can be used include object detection, object tracking, object recognition, object classification, object segmentation, object capture and reconstruction, optical touch, augmented reality presentation, or other applications. Object detection can refer to detecting presence of an object on the mat. Object tracking can refer to tracking movement of the object. Object recognition can refer to identifying a particular object, such as identifying a type of the object, identifying a person, and so forth. Object classification can refer to classifying an object into one of multiple classes or categories. Object segmentation can refer to segmenting an object into multiple segments. Object capture and construction can refer to capturing visual data of an object and constructing a model of the object. Optical touch can refer to recognizing gestures made by a user's hand, a stylus, or other physical artifact that are intended to provide input to a system. The gestures are analogous to gestures corresponding to movement of a mouse device or gestures made on a touch-sensitive display panel. However, optical touch allows the gestures to be made in three-dimensional (3D) space or on a physical target that is not configured to detect user input.

The communications unit in the mat 100 enables the mat 100 to communicate with a plurality of networks and communication links. In some examples, the communications unit of the mat 100 may include a Wi-Fi® interface, a Bluetooth interface, a 3G interface, a 4G interface, a near filed communication (NFC) interface, and/or any other suitable interface that allows the computing device to communicate via one or more networks. The networks may include any suitable type or configuration of network 120 to allow the mat 100 to communicate with any external systems or devices (e.g., the devices 110 and 130).

As mentioned earlier, the display may be a standalone unit or a part of the computing device or may be a part of the mat 100. In either implementation, the display unit may be a transparent an organic light emitting diode (OLED) display, or any other suitable display. The display may be a flexible display that can be wrapped and unwrapped with the mat 100. An attachment section of the display facilitates a coupling of flexible display to a bar in any conventional manner. In one implementation, the flexible display may have a magnetic disclosure, and the display wrapped around the bar may be held in place with the magnetic disclosure. Alternatively, a band may be used to hold the wrapped display around the bar. In various implementations, the flexible display screen may have a variety of structural configuration and material composition. The display may support high display resolutions of 1920×1080, or any other suitable display resolutions. When the display screen supports a 1920×1080 display resolution, 1920 is the total number of pixels across the height of the display 120 and 1080 is the total number of pixels across the height of the display 120. The display is to display content from the application communicated to the mat 100. As discussed above, the display unit may be connected to the mat 100 (if not in the mat) via VGA, HDMI, USB Wi-Fi, Bluetooth, over the local network or over the internet cloud.

It should be noted that the position of the user 140 using the mat 100 is dependent on the type of movement being performed. If the user 140 is measuring force of impact with a slam ball, the feet of the user 140 are close to the outside of the mat 100, not on the mat 100 and the slamming of the ball onto the mat 100 is measured. If the user 140 is measuring the force of a push up or squat jump, then hands or feet of the user 140 are respectively on the mat 100.

In one implementation, as described in detail above, the mat 100 can be used in the health and fitness industry by personal trainers, physical therapists, athletic coaches, and other companies that sell fitness and performance equipment. However, it should be noted that in other implementations, the mat 100 may be utilized for many other areas including, education, gaming, healthcare, and alike. Other examples may be provided while still complying with the principles disclosed herein.

Figure 2:
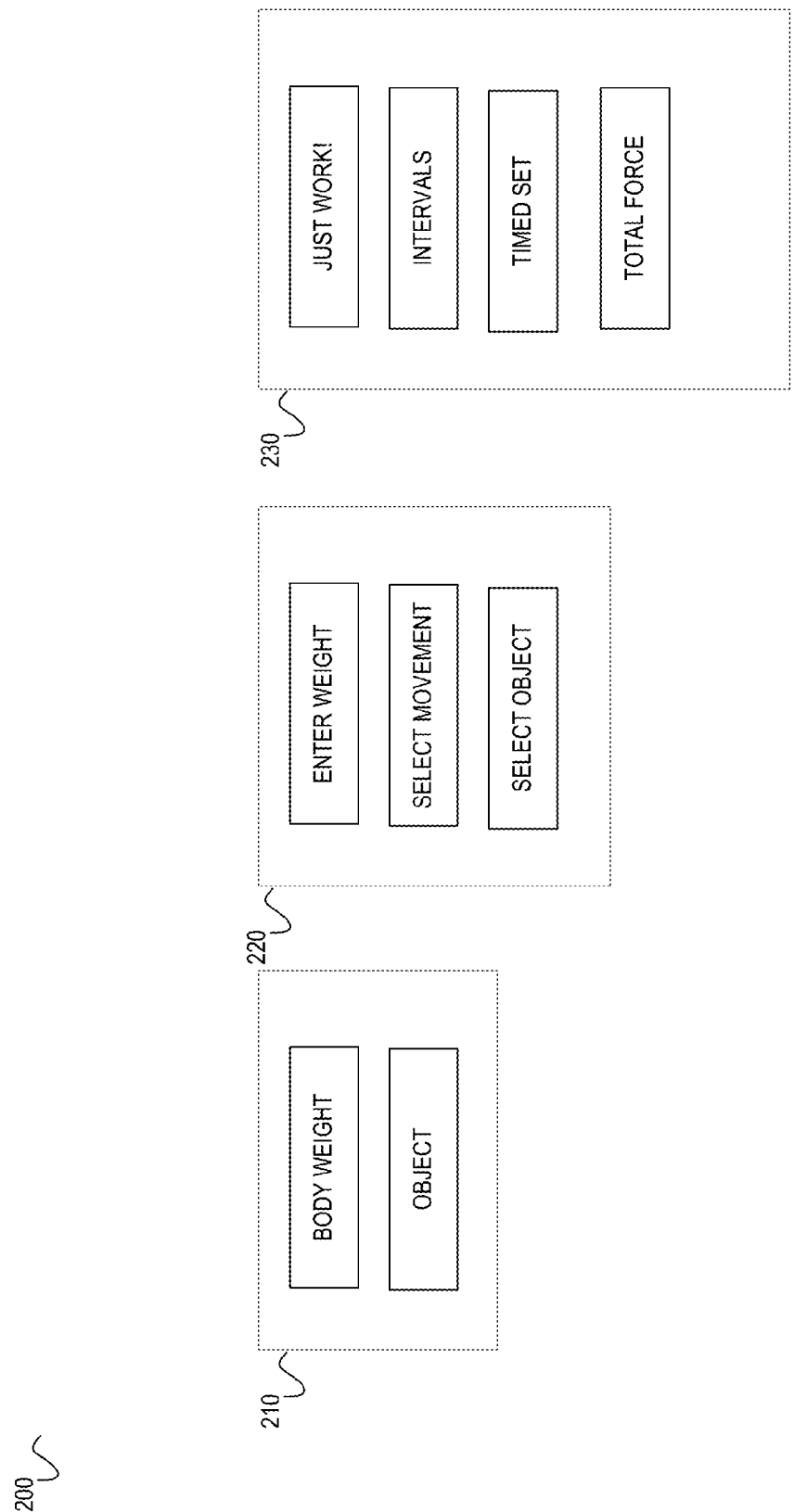
FIG. 2 illustrates an example display unit in accordance with an implementation.
Figure 3:
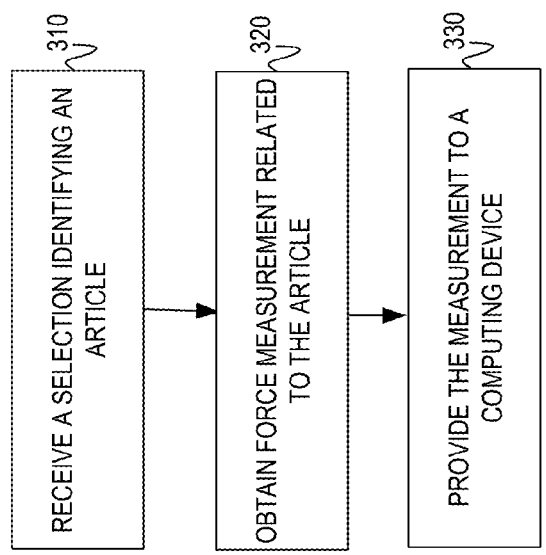
FIG. 3 illustrates an example process flow diagram in accordance with an implementation.

Referring now to FIG. 2, an example user interface of an application 200 running on a computing device associated with a mat in accordance with the principles disclosed herein is shown. Similar to the mat 100 discussed in reference to FIG. 1, the mat in this example is attached to a device, which is running the application 200. In this example, the application 200 allows the user (e.g., the user 140 as shown in FIG. 1) to provide input to set up the application to work with the mat. In box 210, the user selects a body weight or an object. The body weight is selected if the user 140 is measuring the force of a push up or squat jump. The object is selected if the user 140 is measuring force of impact with a slam ball, and the slamming of the ball onto the mat 100 is measured. In box 220, the user enters the body weight or selects a type of object (e.g., ball slam, battle ropes). In addition, the user selects a movement (etc., squat jumps, explosive push-ups, ice skater). In box 230, the user selects various settings that may be related to the intensity and duration of the movement. The mat sensors measure the amount of force of an individual applied through body weight movement and/or applied force through an object.

Turning now to the operation of the mat 100, FIG. 2 depicts a process flow diagram 200 in accordance with an example implementation. It should be readily apparent that the processes depicted in FIG. 2 represent generalized illustrations, and that other processes may be added or the illustrated processes may be removed, modified, or rearranged in many ways. Further, it should be understood that the processes may represent executable instructions stored on memory that may cause a processing device to respond, to perform actions, to change states, and/or to make decisions, for instance. Thus, the described processes may be implemented as executable instructions and/or operations provided by a memory associated with the computing device.

At block 310, the mat receives a selection identifying an article. The article may be an object or a person. At block 320, the mat measures force associated the object or the person. More specifically, the sensor reads the force of impact on the mat 100. The mat sensors measure the amount of force of an individual applied through body weight movement and/or applied force through an object. In one implementation, such force of impact may be by a person (e.g., user 140) using an object or doing a motion (e.g., ball slams, battle ropes, sledgehammer hits, explosive pushups and squats). In another implementation, the force may be from an object such as measuring force of impact with a slam ball. At block 330, the mat provides the measured data to a computing device. Once this data is transferred to the computing device, the application running on the computing device may calculate various metrics such as speed, strength and endurance of the user or the object. Further, the application provides feedback for performance assessment for the user 140.

While the above disclosure has been shown and described with reference to the foregoing examples, it should be understood that other forms, details, and implementations may be made without departing from the spirit and scope of the disclosure that is defined in the following claims.

What is claimed is:

1. An exercise mat, comprising:
   at least one sensor to detect an article on the mat and obtain a force measurement exerted by the article through a movement; and
   a communications unit to communicatively connect the mat to a computing device and provide the force measurement to the computing device,
   wherein the computing device performs a plurality of calculations based on the force measurement.

2. The mat of claim 1, wherein the movement comprises a ball slam, a battle rope, a sledgehammer hit, an explosive pushup or a squat.

3. The mat of claim 1, wherein the article is a person or an object.

4. The mat of claim 1, wherein the computing device comprises a display to present an analysis based on the plurality of calculations.

5. The mat of claim 4, wherein the analysis include total amount of force, average amount of force per movement, and energy used.

6. The mat of claim 4, wherein the computing device and the mat are connected wirelessly.

7. The mat of claim 1, wherein the mat comprises a top layer, a middle layer and a bottom layer, and wherein the at least one sensor and the communications unit are located in the middle layer.

8. The mat of claim 1, wherein the computing device provides a plurality of setting options for a user of the mat.

9. The mat of claim 8, wherein the settings include duration and intensity of the movement.

10. A processor-implemented method for quantifying movements on an exercise mat, comprising:
    receiving a selection identifying an article on the mat;
    obtaining a force measurement exerted by the object through a movement; and
    providing the force measurement to the computing device,
    wherein the computing device performs a plurality of calculations based on the force measurement.

11. The method of claim 10, further comprising displaying an analysis performed based on the plurality of calculations.

12. The method of claim 10, wherein the selection comprises body weight, and the article is a person, and the movement is a jump squat or an explosive pushup or an ice skater.

13. The method of claim 10, wherein the article is an object, and the movement is a ball slam, a battling rope or a sledge hammer.

14. The method of claim 13, wherein the object is controlled by a person, the person being positioned off the mat.

* * * * *